US008659759B2

(12) United States Patent
Koulikov et al.

(10) Patent No.: US 8,659,759 B2
(45) Date of Patent: Feb. 25, 2014

(54) LASER BASED CAVITY ENHANCED OPTICAL ABSORPTION GAS ANALYZER

(75) Inventors: Serguei Koulikov, Mountain View, CA (US); Alexander Kachanov, San Jose, CA (US)

(73) Assignee: Li-Cor, Inc., Licoln, NE (US)

( * ) Notice: Subject to any disclaimer, the term of this patent is extended or adjusted under 35 U.S.C. 154(b) by 215 days.

(21) Appl. No.: 13/218,359

(22) Filed: Aug. 25, 2011

(65) Prior Publication Data

US 2013/0050706 A1    Feb. 28, 2013

(51) Int. Cl.
*G01N 21/00*    (2006.01)

(52) U.S. Cl.
USPC ........... 356/437; 356/469; 356/213; 356/436; 356/72; 73/24.02

(58) Field of Classification Search
USPC .............................. 356/469, 437, 72; 73/24.02
See application file for complete search history.

(56) References Cited

U.S. PATENT DOCUMENTS

| | | | |
|---|---|---|---|
| 3,938,365 A | 2/1976 | Dewey | |
| 4,793,709 A | 12/1988 | Jabr et al. | |
| 5,432,610 A * | 7/1995 | King et al. | 356/432 |
| 5,528,040 A | 6/1996 | Lehmann et al. | |
| 5,544,186 A | 8/1996 | Sauer et al. | |
| 5,912,740 A | 6/1999 | Zare et al. | |
| 5,929,981 A | 7/1999 | Keilbach | |
| 5,973,864 A | 10/1999 | Lehmann et al. | |
| 6,084,682 A | 7/2000 | Zare et al. | |
| 6,233,052 B1 | 5/2001 | Zare et al. | |
| 6,466,322 B1 | 10/2002 | Paldus et al. | |
| 6,504,145 B1 | 1/2003 | Romanini et al. | |
| 6,608,683 B1 | 8/2003 | Pilgrim et al. | |
| 6,618,148 B1 | 9/2003 | Pilgrim et al. | |
| 7,012,696 B2 | 3/2006 | Orr et al. | |
| 7,069,769 B2 | 7/2006 | Kung | |

(Continued)

FOREIGN PATENT DOCUMENTS

| | | |
|---|---|---|
| JP | 07-270308 A | 10/1995 |
| WO | WO 2007/004168 A1 | 11/2007 |
| WO | WO 2008/026189 A1 | 3/2008 |

OTHER PUBLICATIONS

International Search Report and Written Opinion for PCT/US2011/049453 dated Mar. 23, 2012.

(Continued)

*Primary Examiner* — Tarifur Chowdhury
*Assistant Examiner* — Isiaka Akanbi
(74) *Attorney, Agent, or Firm* — Gerald T. Gray; Leydig, Voit & Mayer LLP

(57) ABSTRACT

Cavity enhanced absorption spectroscopy systems and methods for detecting trace gases. When the frequency of laser light approaches the frequency of a resonance cavity mode, the laser begins to fill the cavity to that mode. Optical intensity inside the cavity reflects total cavity loss when the laser light frequency coincides with the cavity mode transmission peak. The intra-cavity optical power also depends on the coupling efficiency of the laser beam to the particular cavity mode. Measurement of intensities of three optical signals, namely, intensity of the light incident on to the cavity, intensity of the light reflected from the cavity, and intensity of the intra-cavity optical power, with their appropriate normalization advantageously significantly reduce effects of baseline calibration and drift as the normalized signal only depends on total cavity loss, and not the coupling efficiency, as in traditional approaches.

28 Claims, 7 Drawing Sheets

(56) References Cited

U.S. PATENT DOCUMENTS

| | | | |
|---|---|---|---|
| 7,245,380 | B2 | 7/2007 | Kosterev |
| 7,259,856 | B2 | 8/2007 | Kachanov et al. |
| 7,398,672 | B2 | 7/2008 | Riddle |
| 7,450,240 | B2 * | 11/2008 | Morville et al. ............ 356/454 |
| 7,535,573 | B2 | 5/2009 | Kachanov et al. |
| 7,569,823 | B2 | 8/2009 | Miller |
| 7,663,756 | B2 | 2/2010 | Cole |
| 7,679,750 | B2 | 3/2010 | Li et al. |
| 7,805,980 | B2 | 10/2010 | Kosterev |
| 7,902,534 | B2 | 3/2011 | Cole et al. |
| 2004/0065816 | A1 | 4/2004 | Ye et al. |
| 2006/0084180 | A1 | 4/2006 | Paldus et al. |
| 2006/0119851 | A1 | 6/2006 | Bounaix |
| 2006/0123884 | A1 | 6/2006 | Selker et al. |
| 2008/0134756 | A1 | 6/2008 | Riddle |
| 2008/0151248 | A1 | 6/2008 | Cole et al. |
| 2008/0196477 | A1 | 8/2008 | Van Herpen |
| 2009/0229345 | A1 | 9/2009 | Van Kesteren |
| 2009/0249861 | A1 | 10/2009 | Van Dijk et al. |
| 2009/0288474 | A1 | 11/2009 | Kalkman et al. |
| 2010/0002234 | A1 | 1/2010 | Cormier et al. |
| 2010/0011836 | A1 | 1/2010 | Kalkman et al. |
| 2010/0296095 | A1 * | 11/2010 | Hong et al. ............ 356/436 |
| 2011/0214479 | A1 | 9/2011 | Kachanov et al. |
| 2011/0295140 | A1 | 12/2011 | Zaidi et al. |

OTHER PUBLICATIONS

Burggraf et al., "Quantitative Photoacoustic Spectroscopy of Intensely Light-Scattering Thermally Thick Samples," Anal. Chem., 1981, vol. 53, pp. 759-764.

Hippler et al., "Cavity-enhanced resonant photoacoustic spectroscopy with optical feedback cw diode lasers: A novel technique for ultratrace gas analysis and high-resolution spectroscopy," The Journal of Chemical Physics, 2010, vol. 133, pp. 044308-1-044308-8.

Cermak, Peter et al., "Optical-Feedback Cavity-Enhanced Absorption Spectroscopy Using a Short-Cavity Vertical-External-Cavity Surface-Emitting Laser," IEEE Photonics Technology Letters, IEEE Service Center, Piscataway, NJ, US, (2010), vol. 22, No. 21, pp. 1607-1609.

Clairon, A. et al., "Frequency Noise Analysis of Optically Self-Locked Diode Lasers," IEEE J. Quantum Electronics, 25(6):1131-1142 (1989).

Courtillot, I. et al., "Sub-ppb $NO^2$ detection by optical feedback cavity-enhanced absorption spectroscopy with a blue diode laser," Applied Physics B, (2006), vol. 85, No. 2-3, pp. 407-412.

Crosson, Eric R. et al., "Stable Isotope Ratios Using Cavity Ring-Down Spectroscopy: Determination of 13C/12C for Carbon Dioxide in Human Breath," Analytical Chemistry, May 1, 2002, vol. 74, No. 9, pp. 2003-2007.

Hamilton, D. J. et al., "A quantum cascade laser-based optical feedback cavity-enhanced absorption spectrometer for the simultaneous measurement of $CH_4$ and $N_2O$ in air," Applied Physics B, (2011), vol. 102, No. 4, pp. 879-890.

Kosterev, A. A. et al., "Quartz-enhanced photoacoustic spectroscopy," Optics Letters 27(21):1902-1904 (Nov. 1, 2002).

Kosterev, A. A. et al., "Trace Humidity Sensor based on Quartz-Enhanced Photoacoustic Spectroscopy," LACSEA 2006, Incline Village, NV, Feb. 5-9, 2006.

Morville, J. et al., "Trace gas detection with DFB lasers and cavity ring-down spectroscopy," SPIE Proc., (2002), vol. 4485, pp. 236-243.

Morville, J. et al., "Effects of laser phase noise on the injection of a high-finesse cavity," Applied Optics, (2002), vol. 41, No. 33, pp. 6980-6990.

Morville, J. et al., "Two schemes for trace detection using cavity ringdown spectroscopy," Applied Physics B, (2004), vol. 78, pp. 465-476.

Morville, J. et al., "Fast, low noise, mode-by-mode, cavity-enhanced absorption spectroscopy by diode-laser self-locking," Applied Physics B, (2005), vol. 80, No. 8, pp. 1027-1038.

Motto-Ros, V. et al., "Extensive characterization of optical feedback cavity enhanced absorption spectroscopy (OF-CEAS) technique: ringdown-time calibration of the absorption scale," Applied Physics B, (2008), vol. 91, No. 1, pp. 203-211.

Romanini, D. et al., "CW cavity ring down spectroscopy," Chemical Physics Letters, (1997), 264, pp. 316-322.

Romanini, D. et al., "Diode laser cavity ring down spectroscopy," Chemical Physics Letters, (1997), 270, pp. 538-545.

Romanini, D. et al., "Measurement of trace gases by diode laser cavity ringdown spectroscopy," Proc. SPIE EUROPTO (Ser. Environmental Sensing), (1999), vol. 3821, pp. 94-104.

Rossi, A. et al., "Optical enhancement of diode laser-photoacoustic trace gas detection by means of external Fabry-Perot cavity," Appl. Phys. Lett. 87, 041110 (2005).

Wehr, R. et al., "Optical feeback cavity-enhanced absorption spectroscopy for in situ measurements of the ratio 13C: 12C in $CO2$," Applied Physics B. (2008), vol. 92, No. 3, pp. 459-465.

* cited by examiner

LASER BASED CAVITY ENHANCED OPTICAL ABSORPTION GAS ANALYZER

BACKGROUND

The present invention relates generally to generally to trace gas detection and more specifically to cavity enhanced absorption spectroscopy systems and methods for measuring the trace gases.

In optical absorption spectroscopy systems and methods, optical intensity inside the resonance cavity reflects total cavity loss at the moment when the laser light frequency coincides with a cavity mode transmission peak. The total cavity loss is a sum of the cavity mirror losses and losses caused by absorption of a gas mixture present in the cavity. However, the intra-cavity optical power depends also on the coupling efficiency of the laser beam to the particular cavity mode. In practice, it is difficult to precisely estimate the coupling efficiency as a lot of parameters affect it, such as spatial, polarization, and spectral overlapping of laser and cavity modes. Moreover, this efficiency can vary over time causing a drift.

In traditional cavity enhanced absorption spectroscopy methods, the intensity of the light transmitted by the cavity is normalized on the intensity of the light incident on to the cavity. In these approaches, all fast non-correlated fluctuations of longitude and transverse intensity modes of the laser beam cause an additional, unwanted noise in the absorption measurements. Also, slow changes of the laser and cavity mode overlapping cause an undesirable drift of the base line.

Therefore it is desirable to provide systems and methods that overcome the above and other problems.

BRIEF SUMMARY

The present invention provides cavity enhanced absorption spectroscopy systems and methods for measuring trace gases with improved measurement capability that is not sensitive to laser-cavity coupling.

In certain embodiments, systems and methods are provided for detecting trace gases using a resonance optical cavity, containing a gas mixture, that has two or more mirrors and that is capable of being frequency-scanned by changing the optical length of the cavity. A laser or other light source that is capable of being frequency-scanned is coupled to the cavity though one of the cavity mirror, e.g., a "coupling mirror". When the frequency of the laser light approaches the frequency of one of the cavity modes, the laser begins to fill the cavity to that mode. Optical intensity inside the resonance cavity reflects total cavity loss at the moment when the laser light frequency coincides with the cavity mode transmission peak. The total cavity loss is a sum of the cavity mirror losses and losses caused by absorption of analyzed gas mixture. The intra-cavity optical power depends also on the coupling efficiency of the laser beam to the particular cavity mode. In certain embodiments, measurement of intensities of three optical signals, namely, intensity of the light incident on to the cavity, intensity of the light reflected from the cavity, and intensity of the intra-cavity optical power, with their appropriate normalization advantageously significantly reduce the above unwanted effects. In contrast to the traditional approaches, the difference between the intensity of the light incident on to the cavity and the intensity of the light reflected from the cavity is normalized on the intensity of the intra-cavity optical power. If the cavity length is chosen to remove a degeneracy of high order transverse modes, than the only one longitude and transverse laser mode can be coupled to the particular cavity mode at that time. All other laser modes are reflected from the cavity and canceled out in the numerator. Hence, the only laser mode which is coupled to the cavity affects both numerator and denominator, and the ratio depends only on total cavity loss.

According to one aspect of the present invention, a system for detecting one or more analyte species present in a gaseous or liquid medium is provided. The system typically includes a laser that emits continuous wave laser light, a resonant optical cavity containing the medium and having at least two cavity mirrors, one of which is a cavity coupling mirror, and mode matching optics configured to couple the laser light to the cavity via the cavity coupling mirror. The system also typically includes a detector subsystem configured to generate first, second and third signals representing an intensity of the laser light incident on the cavity coupling mirror, an intensity of the laser light reflected by the cavity coupling mirror, and an intensity of the intracavity optical power of light circulating in the cavity, respectively. The system also typically includes an intelligence module adapted to process the first, second and third signals to produce a normalized signal that is a linear function of total cavity loss and that is not sensitive to laser-cavity coupling.

According to another aspect of the present invention, a system for detecting one or more analyte species present in a gaseous or liquid medium is provided. The system typically includes a laser that emits continuous wave laser light, a resonant optical cavity containing the medium and having at least two cavity mirrors, one of which is a cavity coupling mirror, and mode matching optics configured to couple the laser light to the cavity via the cavity coupling mirror. The system also typically includes a first detector configured to measure an intensity of the laser light incident on the cavity coupling mirror and to generate a first signal representing the intensity of the laser light incident on the cavity coupling mirror, and a second detector configured to measure an intensity of the laser light reflected by the cavity coupling mirror and to generate a second signal representing the intensity of the laser light reflected by the cavity coupling mirror, and a third detector configured to measure an intensity of the intracavity optical power of light circulating in the cavity and to generate a third signal representing the intracavity optical power of light circulating in the cavity. The system also typically includes an intelligence module adapted to process the first, second and third signals to produce a normalized signal that is a linear function of total cavity loss and that is not sensitive to laser-cavity coupling.

According to yet another aspect of the present invention, a method is provided for detecting one or more analyte species present in a gaseous or liquid medium using a laser that that emits continuous wave laser light and a resonant optical cavity containing the medium and having at least two cavity mirrors, one of which is a cavity coupling mirror. The method typically includes coupling the laser light to the cavity via the cavity coupling mirror using mode matching optics, measuring an intensity of the laser light incident on the cavity coupling mirror and generating a first signal representing the intensity of the laser light incident on the cavity coupling mirror, measuring an intensity of the laser light reflected by the cavity coupling mirror and generating a second signal representing the intensity of the laser light reflected by the cavity coupling mirror, and measuring an intensity of the intracavity optical power of light circulating in the cavity and generating a third signal representing the intensity of the intracavity optical power of light circulating in the cavity. The method also typically includes processing the first, second and third signals to produce a normalized signal that is a linear function of total cavity loss and that is not sensitive to laser-cavity coupling.

According to yet a further aspect of the present invention, a system for detecting one or more analyte species present in a gaseous or liquid medium is provided. The system typically includes a laser that emits continuous wave laser light, a resonant optical cavity defined by at least two cavity mirrors, one of which is a cavity coupling mirror, wherein the medium is located within the cavity, and mode matching optics configured to couple the laser light to the cavity via the cavity coupling mirror. The system also typically includes a first means for measuring an intensity of the laser light incident on the cavity coupling mirror and for generating a first signal representing the intensity of the laser light incident on the cavity coupling mirror, a second means for measuring an intensity of the laser light reflected by the cavity coupling mirror and for generating a second signal representing the intensity of the laser light reflected by the cavity coupling mirror, and a third means for measuring an intensity of the intracavity optical power of light circulating in the cavity and for generating a third signal representing the intracavity optical power of light circulating in the cavity. The system also typically includes a means for processing signals received from the first, second and third means for measuring to produce a normalized signal that is a linear function of total cavity loss and that is not sensitive to laser-cavity coupling.

In certain aspects, the third detector includes a photodetector located external to the cavity. In certain aspects, the external photodetector obtains or produces a signal proportional to the intracavity optical power by detecting the intensity of light emerging from a cavity mirror. In certain aspects, the third detector includes a photodetector located internal to the cavity. In certain aspects, the internal photodetector obtains or produces a signal proportional to the intracavity optical power by detecting the intensity of light scattered by one of the cavity mirrors. In certain aspects, the internal photodetector obtains or produces a signal proportional to the intracavity optical power by detecting the intensity of light scattered by the medium within the cavity.

In certain aspects, the cavity is one of a ring cavity having three or more cavity mirrors, a linear cavity having two cavity mirrors, or a V-shaped cavity having three cavity mirrors. In certain aspects, the cavity is capable of being scanned whereby an optical frequency of a cavity resonance peak is adjustable over a range of frequencies, e.g., using a means for controlling a position of one of the cavity mirrors so as to scan the optical frequency of the cavity resonance peak. In certain aspects, the laser is capable of being scanned whereby a mean optical frequency of the laser is adjustable over a range of frequencies, e.g., using a means for adjusting the mean optical frequency of the laser so as to scan the mean optical frequency of the laser over a cavity resonance peak. In certain aspects, the intelligence module produces the normalized signal by calculating a ratio of the difference between the intensity of the laser light incident on the cavity coupling mirror and the intensity of the laser light reflected by the cavity coupling mirror to the intensity of the intracavity optical power of light circulating in the cavity.

In certain aspects, a means for controlling a position of one of the cavity mirrors is provided so as to scan the optical frequency of the cavity resonance peak, e.g., while maintaining a lock between a mean optical frequency of the laser and the cavity resonance peak.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 7($b$) shows the normalized transmitted signal vs. the round-trip cavity loss; and FIG. 7($c$) shows the normalized signal, which is a linear function of the cavity loss caused by gas absorption.

DETAILED DESCRIPTION

The present invention provides cavity enhanced absorption spectroscopy systems and methods for measuring trace gases with improved measurement capability that is not sensitive to laser-cavity coupling.

Figure 2:
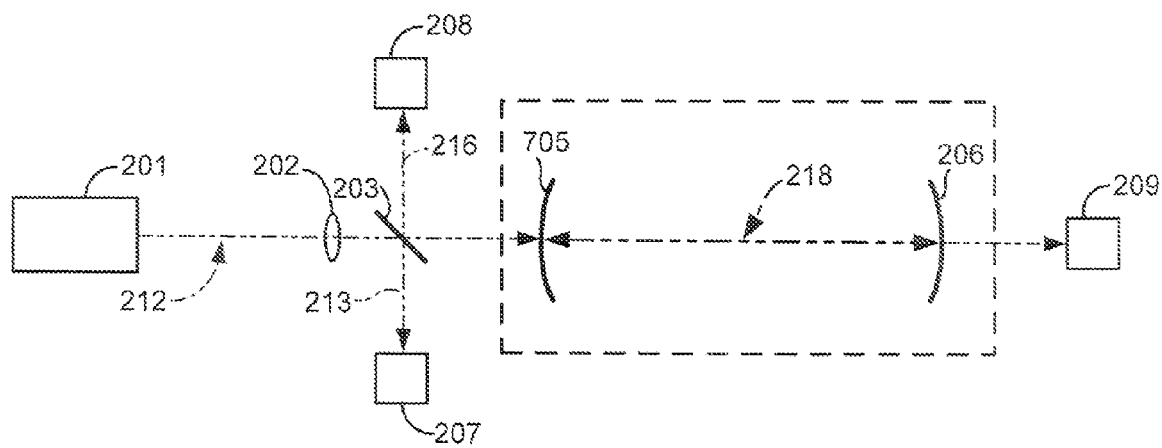
FIG. 2 illustrates a CEAS system having a linear cavity configuration according to another embodiment.
Figure 3:
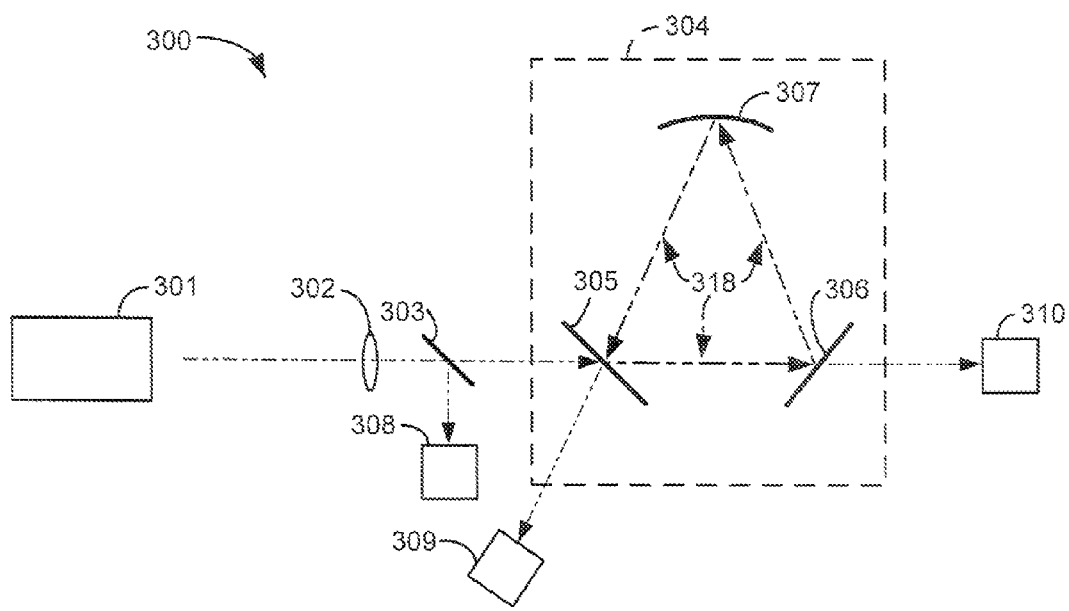
FIG. 3 illustrates a CEAS system having a ring-shaped cavity configuration according to another embodiment.

Embodiments of the present invention provide simple, precise and reliable cavity enhanced absorption spectroscopy systems and methods for detecting trace gases that has higher sensitivity, accuracy and stability as compared to existing systems and methods based upon similar principles. This is achieved by measuring three optical signals, a combination of which completely characterizes the total cavity. Embodiments of the present invention significantly simplify the baseline calibration problem, as the normalized signal only depends on total cavity loss, and not the coupling efficiency, as in traditional approaches. For example, three different exemplary configurations shown in FIGS. 1-3 are designed to allow for measuring three optical signals, which characterize the cavity loss of: a 3-mirror V-cavity (FIG. 1), a 2-mirror linear cavity (FIG. 2), and a ring cavity (FIG. 3).

Figure 1:
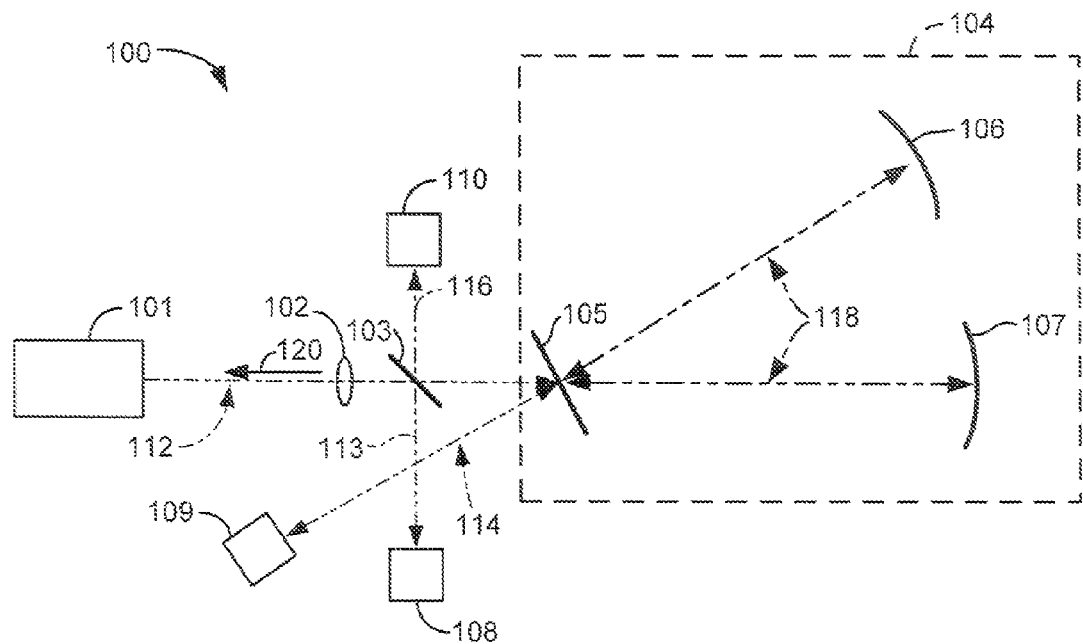
FIG. 1 illustrates a cavity enhanced absorption spectroscopy (CEAS) system having a v-shaped cavity configuration according to one embodiment.

FIG. 1 illustrates a cavity enhanced absorption spectroscopy (CEAS) system 100 according to one embodiment. As shown, CEAS system 10 includes a light source 101 that emits continuous wave coherent light, such as continuous wave laser light, an optical cavity 104 and three detectors (108, 109 and 110). As shown, cavity 104 is a V-shaped cavity defined by cavity coupling mirror 105 and mirrors 106 and 107. An enclosure or housing (not shown) provides an air tight seal for cavity 104 such as to allow control of the environment within the housing and hence the cavity 104. One or more optical components 102 are configured and arranged to facilitate directing laser light from source 101 to the optical cavity 104 via cavity coupling mirror 105. In the embodiment shown in FIG. 1, a beam splitting element 103 is positioned and aligned so as to allow substantially all of the incident light 112 emitted or generated by source 101 to impinge on cavity coupling mirror 105. A portion of the incident light beam 112 is directed (e.g., reflected or refracted) by element 103 to detector 108. Cavity coupling mirror 105, in this embodiment, is arranged at an angle with respect to beam 112 such that a portion of incident light 112 is reflected off of mirror 105 as reflected beam 114 and detected by detector 109. A portion of incident light 112 enters cavity 104 via mirror 105. Depending on the frequency of incident light 112 and the optical length of cavity 104 (e.g., optical length from mirror 107 to mirror 105 to mirror 106) light 118 circulating in the cavity may build up and resonate at one or a plurality of cavity modes. A portion of the intra-cavity light 118 circulating in cavity 104 between mirror 107, 105 and 106, emerges or escapes via mirror 105 and impinges on element 103. Element 103 directs a portion 116 to detector 110 and allows a portion 120 to pass back to source 101.

In certain aspects, source 101 includes a laser or other coherent light source that is sensitive or responsive to optical feedback. One useful laser is a semiconductor diode laser that is sensitive to optical feedback from light 120 impinging on the laser from the cavity coupling mirror 105. Other laser sources might include diode lasers, quantum cascade lasers and solid state lasers. Selection of the reflectivities of mirrors 105, 106 and 107 defines the optical feedback intensity. Source 101 is also preferably capable of being frequency scanned, whereby a mean optical frequency of the laser is adjustable over a range of frequencies. This can be accomplished as is well known, such as, for example, by adjusting the current applied to a diode laser and/or adjusting a temperature of the laser medium. In certain aspects, the cavity 104 is also capable of being frequency scanned, e.g., by changing or adjusting an optical length of the cavity, whereby an optical frequency of a cavity resonance peak is adjustable over a range of frequencies. Adjustment of the optical length of the cavity can include adjusting a relative position of one or more of the cavity mirrors, adjusting a pressure of the medium within cavity 104.

In certain embodiments, CEAS system 100 is useful for detecting trace gases within a gas mixture present in the cavity 104. When the frequency of the light 112 emitted by source 101 approaches the frequency of one of the cavity modes, the light 112 entering the cavity 104 begins to fill the cavity to that mode. The optical intensity of the light 118 circulating inside the resonance cavity reflects total cavity loss at the moment when the light frequency of light 112 coincides with the cavity mode transmission peak. The total cavity loss is a sum of the cavity mirror losses and losses caused by absorption by the gas mixture present in the cavity. However, the intra-cavity optical power depends also on the coupling efficiency of the light beam 112 to the particular cavity mode. In practice, it may be difficult to precisely estimate the coupling efficiency, because a lot of parameters affect the efficiency, such as spatial, polarization, and spectral overlapping between laser and cavity modes. Moreover, this efficiency can vary over time causing a drift. In traditional cavity enhanced absorption spectroscopy methods, the intensity of the light transmitted by the cavity is normalized on the intensity of the light incident on to the cavity. In this approach, all fast non-correlated fluctuations of the longitude and transverse modes of intensities of the laser beam cause an additional noise in the absorption measurements. Slow changes of the laser and cavity mode overlapping cause a drift of base line.

However, according to certain embodiments, measurement of intensities of three optical signals, namely, the intensity of the light incident on to the cavity, the intensity of the light reflected from the cavity, and the intensity of the intra-cavity optical power, with their appropriate normalization can significantly reduce the above unwanted effects. In contrast to the traditional approach, in certain embodiments, the difference between the intensity of the light incident on to the cavity and the intensity of the light reflected from the cavity is normalized on the intensity of the intra-cavity optical power. If the cavity length is chosen to remove a degeneracy of high order transverse modes, then the only one longitude and transverse laser mode can be coupled to the particular cavity mode at that time. All other laser modes are reflected from the cavity and canceled out in the numerator. So, the only laser mode which is coupled to the cavity affects both numerator and denominator, and hence the ratio depends only on total cavity loss.

Hence, in operation according to one embodiment, detector 108 detects and generates a signal representing the intensity of the laser light 112 incident on the cavity coupling mirror 105, detector 109 detects and generates a signal representing the intensity of the laser light reflected by the cavity coupling mirror 105, and detector 110 detects and generates a signal representing the intra-cavity optical power of light circulating in the cavity 104. An intelligence module (not shown) communicably coupled with the three detectors, receives the three detector output signals and processes these signals to produce or generate a normalized signal that is a linear function of total cavity loss and that is not sensitive to laser-cavity coupling.

Different approaches for measurement of intra-cavity optical power are shown in FIGS. 2-6 and 8-10. Like element numbers generally indicate identical or functionally similar elements. For example source 101 and sources 201 and 301, etc, are generally functionally similar or identical.

FIG. 2 illustrates a cavity enhanced absorption spectroscopy (CEAS) system 200 according to another embodiment. The principle of operation of CEAS system 200 is similar to that of CEAS system 100, however, the cavity 204 of CEAS 200 is a linear cavity including only two cavity mirrors 205 and 206, with cavity mirror 205 being a cavity coupling mirror. Cavity coupling mirror 205 is positioned such that incident light beam 212 generated by source 201 impinges upon mirror 105 perpendicular to the plane defined by mirror 205 at the area of impact. Beamsplitting element 203 directs a portion 213 of incident beam 212 to detector 207 and element 203 also directs a portion 216 of light reflected by mirror 205 to detector 208. Detector 209 is positioned to receive and detect the portion of the intra-cavity light 218 circulating in cavity 204 between mirror 205 and 206 that emerges or escapes via mirror 206. Similar to the operation of CEAS 100, detector 207 detects and generates a signal representing the intensity of the laser light 212 incident on the cavity coupling mirror 205, detector 208 detects and generates a signal representing the intensity of the laser light reflected by the cavity coupling mirror 205, and detector 209 detects and generates a signal representing the intra-cavity optical power of light circulating in the cavity. An intelligence module (not shown) receives the three detector output signals and processes these signals to produce or generate a normalized signal that is a linear function of total cavity loss and that is not sensitive to laser-cavity coupling.

FIG. 3 illustrates a cavity enhanced absorption spectroscopy (CEAS) system 300 according to another embodiment. The principle of operation of CEAS system 300 is similar to that of CEAS system 100, however, the cavity 304 of CEAS 300 is a ring cavity including three cavity mirrors 305, 306 and 307, with cavity mirror 305 being a cavity coupling mirror. It should be appreciated that greater than 3 mirrors may be used to form a ring cavity structure. Cavity coupling mirror 305 is positioned such that incident light beam 312 generated by source 301 impinges upon mirror 305 at an angle relative to the plane defined by mirror 305 at the area of impact so that light is reflected to detector 309. Beamsplitting element 303 directs a portion 313 of incident beam 312 to detector 308. Detector 310 is positioned to receive and detect the portion of the intra-cavity light 318 circulating within cavity 304 between mirrors 305, 306 and 307 in a ring fashion that emerges or escapes via mirror 306. It should be appreciated that detector 310 may be positioned to detect light emerging from mirror 307. Similar to the operation of CEAS 100, detector 308 detects and generates a signal representing the intensity of the laser light 312 incident on the cavity coupling mirror 305, detector 309 detects and generates a signal representing the intensity of the laser light reflected by the cavity coupling mirror 305, and detector 310 detects and generates a signal representing the intra-cavity optical power of light circulating in the cavity 304. An intelligence module (not shown) receives the three detector output signals and processes these signals to produce or generate a normalized signal that is a linear function of total cavity loss and that is not sensitive to laser-cavity coupling.

Figure 4:
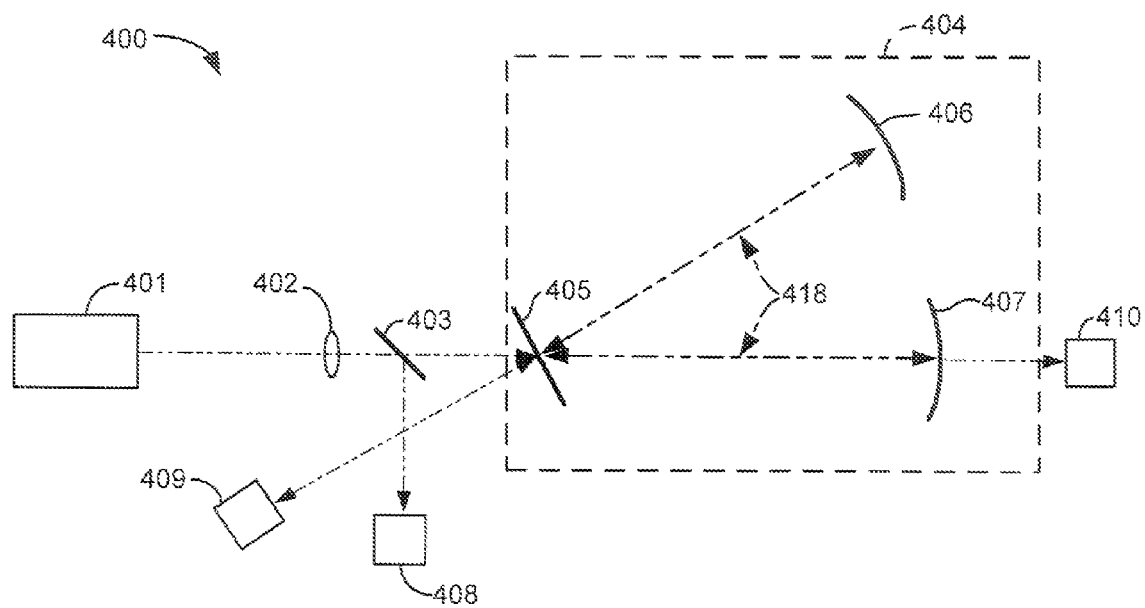
FIG. 4 illustrates a CEAS system having a v-shaped cavity configuration according to another embodiment.

FIG. 4 illustrates a cavity enhanced absorption spectroscopy (CEAS) system 400 according to yet another embodiment. The principle of operation of CEAS system 400 is similar to that of CEAS system 100, including an identical cavity structure 404, with cavity mirror 405 being a cavity coupling mirror. Cavity coupling mirror 405 is positioned such that incident light beam 412 generated by source 401 impinges upon mirror 405 at an angle relative to the plane defined by mirror 405 at the area of impact so that light is reflected to detector 409. Beamsplitting element 403 directs a portion 413 of incident beam 412 to detector 408. Detector 410, in this embodiment, is positioned to receive and detect the portion of the intra-cavity light 418 circulating back and forth within cavity 404 between mirrors 405, 406 and 407 that emerges or escapes via mirror 407. It should be appreciated that detector 410 may be positioned to detect light emerging from mirror 406. Similar to the operation of CEAS 100, detector 408 detects and generates a signal representing the intensity of the laser light 412 incident on the cavity coupling mirror 405, detector 409 detects and generates a signal representing the intensity of the laser light reflected by the cavity coupling mirror 405, and detector 410 detects and generates a signal representing the intracavity optical power of light circulating in the cavity 404. An intelligence module (not shown) receives the three detector output signals and processes these signals to produce or generate a normalized signal that is a linear function of total cavity loss and that is not sensitive to laser-cavity coupling.

Figure 5:
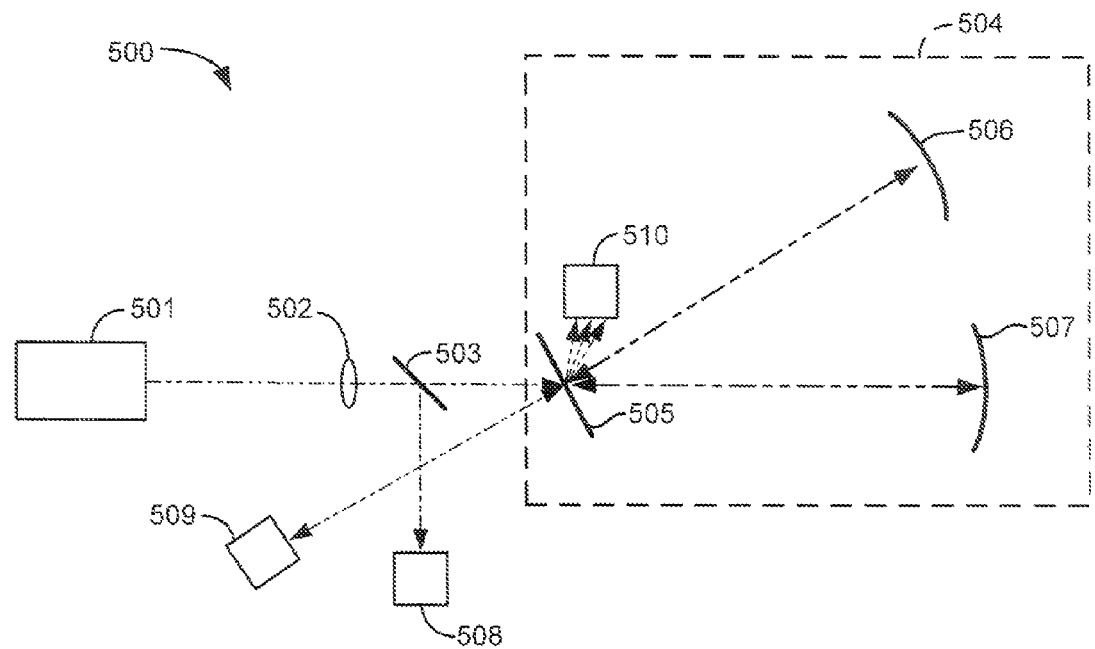
FIG. 5 illustrates a CEAS system having a v-shaped cavity configuration according to another embodiment.

FIG. 5 illustrates a cavity enhanced absorption spectroscopy (CEAS) system 500 according to yet a further embodiment. The principle of operation of CEAS system 500 is similar to that of CEAS system 100 or 400, including a v-shaped cavity structure 504, with cavity mirror 505 being a cavity coupling mirror. Cavity coupling mirror 505 is positioned such that incident light beam 512 generated by source 501 impinges upon mirror 505 at an angle relative to the plane defined by mirror 505 at the area of impact so that light is reflected to detector 509. Beamsplitting element 503 directs a portion 513 of incident beam 512 to detector 508. Detector 510, in this embodiment, is positioned internal to the cavity (e.g., within the cavity housing structure) to detect an intensity of the intra-cavity light 518 circulating back and forth within cavity 504 between mirrors 505, 506 and 507 by measuring the intensity of the light scattered by cavity mirror 505. It should be appreciated that detector 510 may also be positioned to detect light scattered by mirror 506 and/or 507. Similar to the operation of CEAS 100, detector 508 detects and generates a signal representing the intensity of the laser light 512 incident on the cavity coupling mirror 505, detector 509 detects and generates a signal representing the intensity of the laser light reflected by the cavity coupling mirror 505, and detector 510 detects scattered light and generates a signal representing the intra-cavity optical power of light circulating in the cavity 504. An intelligence module (not shown) receives the three detector output signals and processes these signals to produce or generate a normalized signal that is a linear function of total cavity loss and that is not sensitive to laser-cavity coupling.

Figure 6:
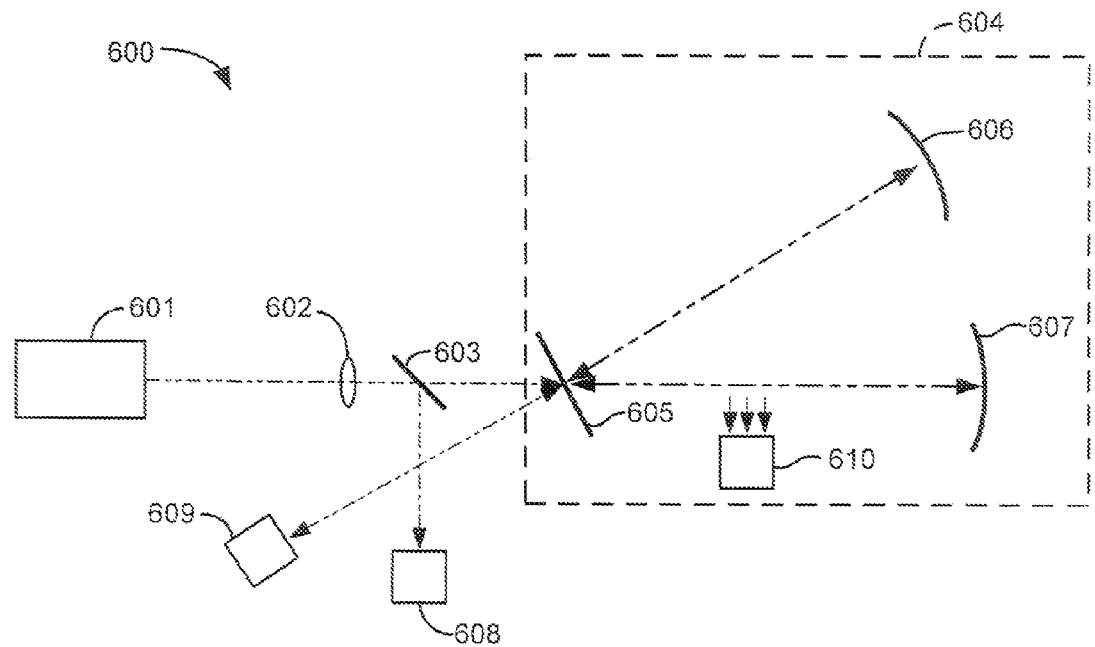
FIG. 6. illustrates a CEAS system having a v-shaped cavity configuration according to another embodiment.

FIG. 6 illustrates a cavity enhanced absorption spectroscopy (CEAS) system 600 according to yet a further embodiment. The principle of operation of CEAS system 600 is similar to that of CEAS system 100 or 500, including a v-shaped cavity structure 604, with cavity mirror 605 being a cavity coupling mirror. Cavity coupling mirror 605 is positioned such that incident light beam 612 generated by source 601 impinges upon mirror 605 at an angle relative to the plane defined by mirror 605 at the area of impact so that light is reflected to detector 609. Beamsplitting element 603 directs a portion 613 of incident beam 612 to detector 608. Detector 610, in this embodiment, is positioned internal to the cavity (e.g., within the cavity housing structure) to detect an intensity of the intra-cavity light 618 circulating back and forth within cavity 604 between mirrors 605, 606 and 607 by measuring the intensity of the light scattered by the gas mixture filling the optical cavity 604. Such scattering effects may include static or Rayleigh scattering, or may be the result of, for example, Raman scattering. Similar to the operation of CEAS 100 or CEAS 500, detector 608 detects and generates a signal representing the intensity of the laser light 612 incident on the cavity coupling mirror 605, detector 609 detects and generates a signal representing the intensity of the laser light reflected by the cavity coupling mirror 605, and detector 610 detects scattered light and generates a signal representing the intracavity optical power of light circulating in the cavity 604. An intelligence module (not shown) receives the three detector output signals and processes these signals to produce or generate a normalized signal that is a linear function of total cavity loss and that is not sensitive to laser-cavity coupling.

In certain embodiments, each detector element includes a photodetector, and associated electronics, for detecting light and outputting a signal representing the detected light. Examples of useful photodetectors might include silicon, InGaAs, Ge or GAP based photodetectors.

Figure 7A:
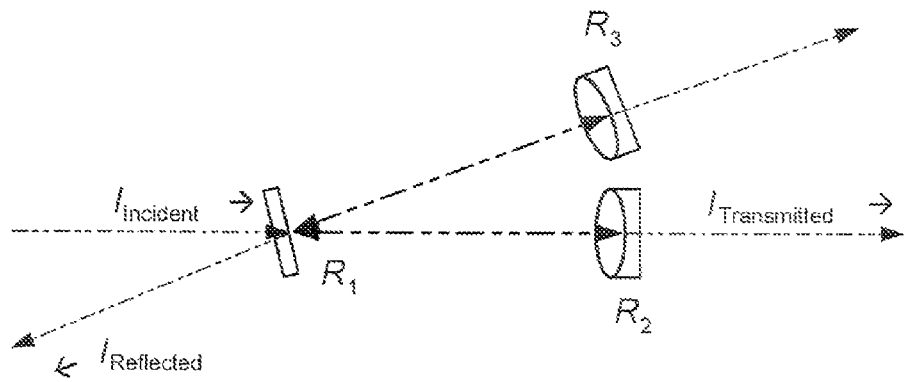
FIG. 7($a$) illustrates an example of a three mirror V-cavity with specific mirror element reflectivites as shown.
Figure 7B:
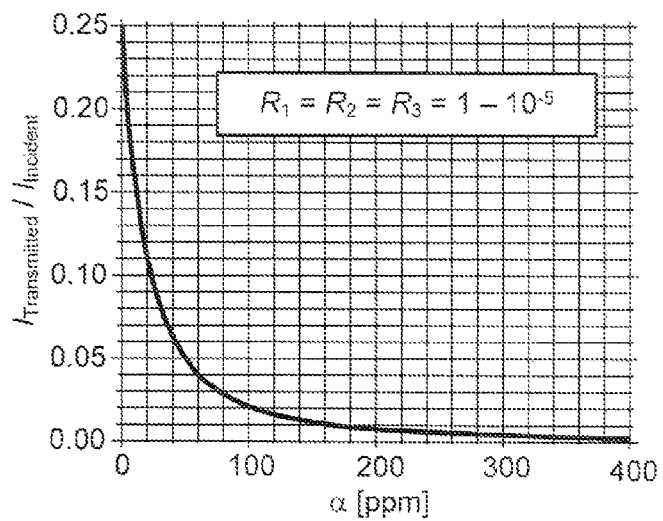
Figure 7C:
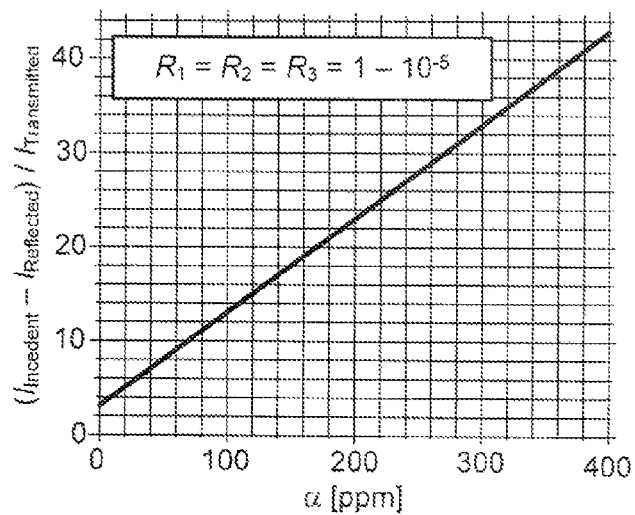

FIG. 7. (a) illustrates a specific example of a three mirror V-cavity where the mirror reflectivities R1, R2, and R3 are each equal to about $1-10^{-5}$; FIG. 7(b) shows the normalized transmitted signal vs. the round-trip cavity loss; and FIG. 7(c) shows the normalized signal, which is a linear function of the cavity loss caused by gas absorption. Here, R1, R2, and R3 are the mirror reflectivities, and $\alpha$ is the round-trip cavity loss caused by gas absorption expressed in parts per million units. As will be appreciated, different mirror reflectivities are contemplated for the various embodiments discussed herein.

Figure 8:
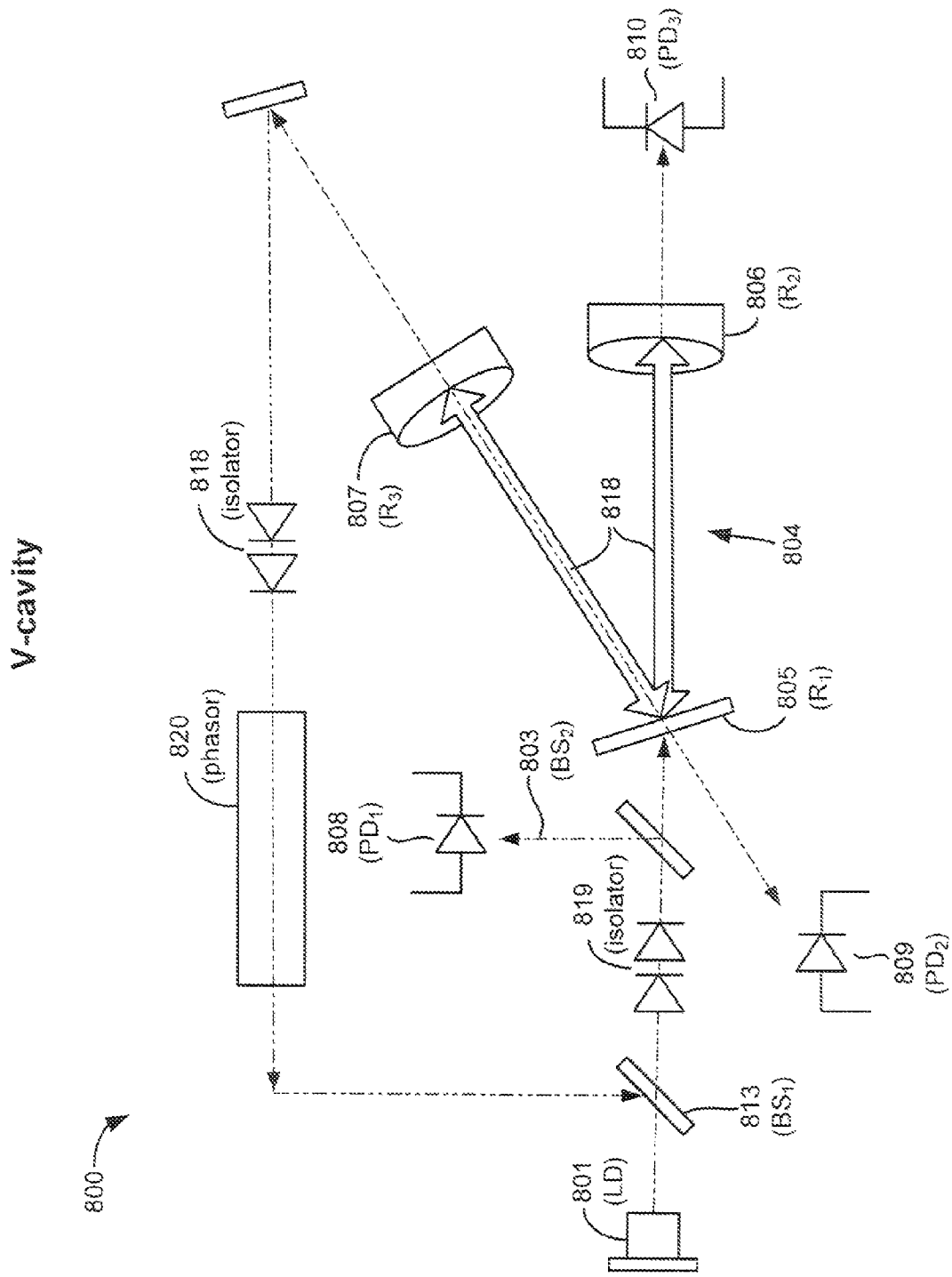
FIG. 8. illustrates a CEAS system having a v-shaped cavity configuration according to another embodiment.

FIG. 8 illustrates a cavity enhanced absorption spectroscopy (CEAS) system 800 according to yet another embodiment. The principle of operation of CEAS system 800 is similar to that of CEAS system 100 and 400, for example, including a v-shaped cavity structure 804, with cavity mirror 805 being a cavity coupling mirror. Cavity coupling mirror 805 is positioned such that incident light beam 812 generated by laser diode source 801 impinges upon mirror 805 at an angle relative to the plane defined by mirror 805 at the area of impact so that light is reflected to photodetector 809. Beamsplitting element 803 directs a portion 813 of incident beam 812 to detector 808. Photodetector 810, in this embodiment, is positioned to receive and detect the portion of the intracavity light 818 circulating back and forth within cavity 804 between mirrors 805, 806 and 807 that emerges or escapes via mirror 806. Similar to the operation of CEAS 100, photodetector 808 detects and generates a signal representing the intensity of the laser light 812 incident on the cavity coupling mirror 805, detector 809 detects and generates a signal representing the intensity of the laser light reflected by the cavity coupling mirror 805, and detector 810 detects and generates a signal representing the intracavity optical power of light circulating in the cavity 804. An intelligence module (not shown) receives the three detector output signals and processes these signals to produce or generate a normalized signal that is a linear function of total cavity loss and that is not sensitive to laser-cavity coupling.

Also as shown in FIG. 8 are additional elements to enhance control of the optical feedback, specifically control of the optical feedback to source 801. As shown, light emerging from cavity mirror 807 passes through a phasor 820 (or other adjustable light attenuating element) and returns to source 801, via beamsplitting element 813. Optical isolators 818 and 819 are provided to completely block light which travels in the opposite direction. For example, optical isolator element 819 blocks light returning (e.g., reflected light or light escaping from the cavity via mirror 805) from mirror 805 toward source 801, and optical isolator element 818 prevents light returning from phasor 820 (e.g., light reflected by phasor 820 or source light reflected by beamsplitter 813 that is passing through phasor 820 on an opposite path) from impinging on mirror 807. Selection of the cavity mirror reflectivities (e.g., $R_1$, $R_2$ and $R_3$) defines the optical feedback intensity provided to source 801. Use of phasor 820 advantageously allows for phase control of the optical feedback provided to source 801 from the cavity 804.

Figure 9:
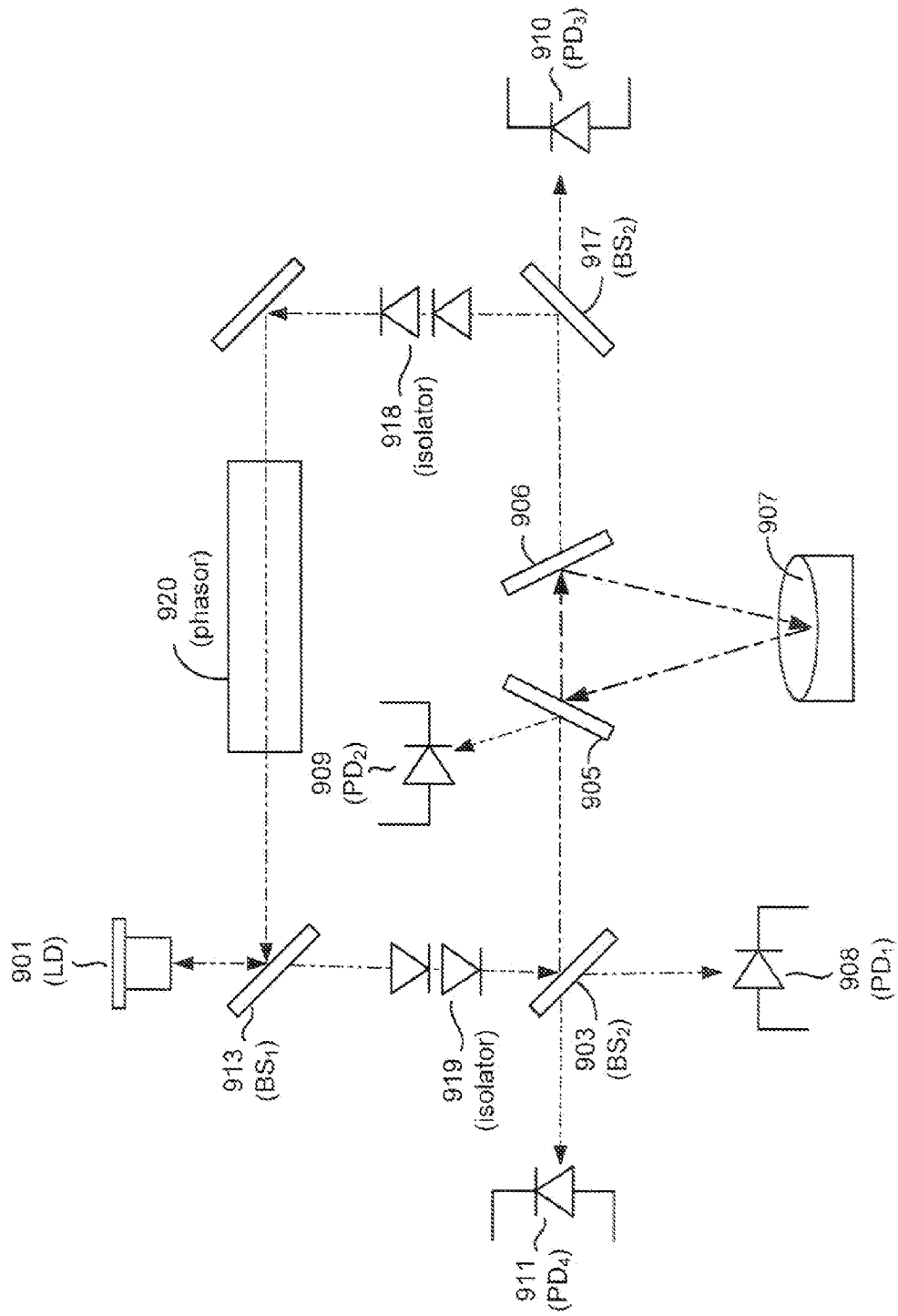
FIG. 9. illustrates a CEAS system having a ring-shaped cavity configuration according to another embodiment.

FIG. 9 illustrates a cavity enhanced absorption spectroscopy (CEAS) system 900 according to yet another embodiment. The principle of operation of CEAS system 900 is similar to that of CEAS system 100 and 300, for example, including a ring-shaped cavity structure 904, with cavity mirror 905 being a cavity coupling mirror. Cavity coupling mirror 905 is positioned such that incident light beam 912 generated by laser diode source 901 impinges upon mirror 905 at an angle relative to the plane defined by mirror 905 at the area of impact so that light is reflected to photodetector 909. Beamsplitting element 903 allows a portion 913 of incident beam 912 to pass to detector 908 and reflects the remainder to mirror 905. Photodetector 910, in this embodiment, is positioned to receive and detect the portion of the intracavity light 918 circulating within cavity 804 between mirrors 905, 906 and 907 that emerges or escapes via mirror 906. Similar to the operation of CEAS 100, photodetector 908 detects and generates a signal representing the intensity of the laser light 912 incident on the cavity coupling mirror 905, detector 909 detects and generates a signal representing the intensity of the laser light reflected by the cavity coupling mirror 905, and detector 910 detects and generates a signal representing the intracavity optical power of light circulating in the cavity 904. An intelligence module (not shown) receives the three detector output signals and processes these signals to produce or generate a normalized signal that is a linear function of total cavity loss and that is not sensitive to laser-cavity coupling.

Also as shown in FIG. 9 are additional elements to enhance control of the optical feedback, specifically control of the optical feedback to source 901. As shown, a portion of light emerging from cavity mirror 906 is directed by beamsplitting element 917 through a phasor 920 (or other adjustable light attenuating element) and returns to source 901, via beamsplitting element 913. Optical isolators 918 and 919 are provided to completely block light which travels in the opposite direction. For example, optical isolator element 919 blocks light returning (e.g., reflected light or light escaping from the cavity via mirror 905) from mirror 905 toward source 901 and optical isolator element 918 prevents light returning from phasor 920 (e.g., light reflected by phasor 920 or source light reflected by beamsplitter 913 that is passing through phasor 920 on an opposite path) from impinging on mirror 907. Selection of the cavity mirror reflectivities (e.g., $R_1$, $R_2$ and $R_3$) defines the optical feedback intensity provided to source 901. Use of phasor 920 advantageously allows for phase control of the optical feedback provided to source 901 from the cavity 904. Additional photodetector 911 is provided to measure, e.g., an intensity of the light circulating backward in the ring cavity.

Figure 10:
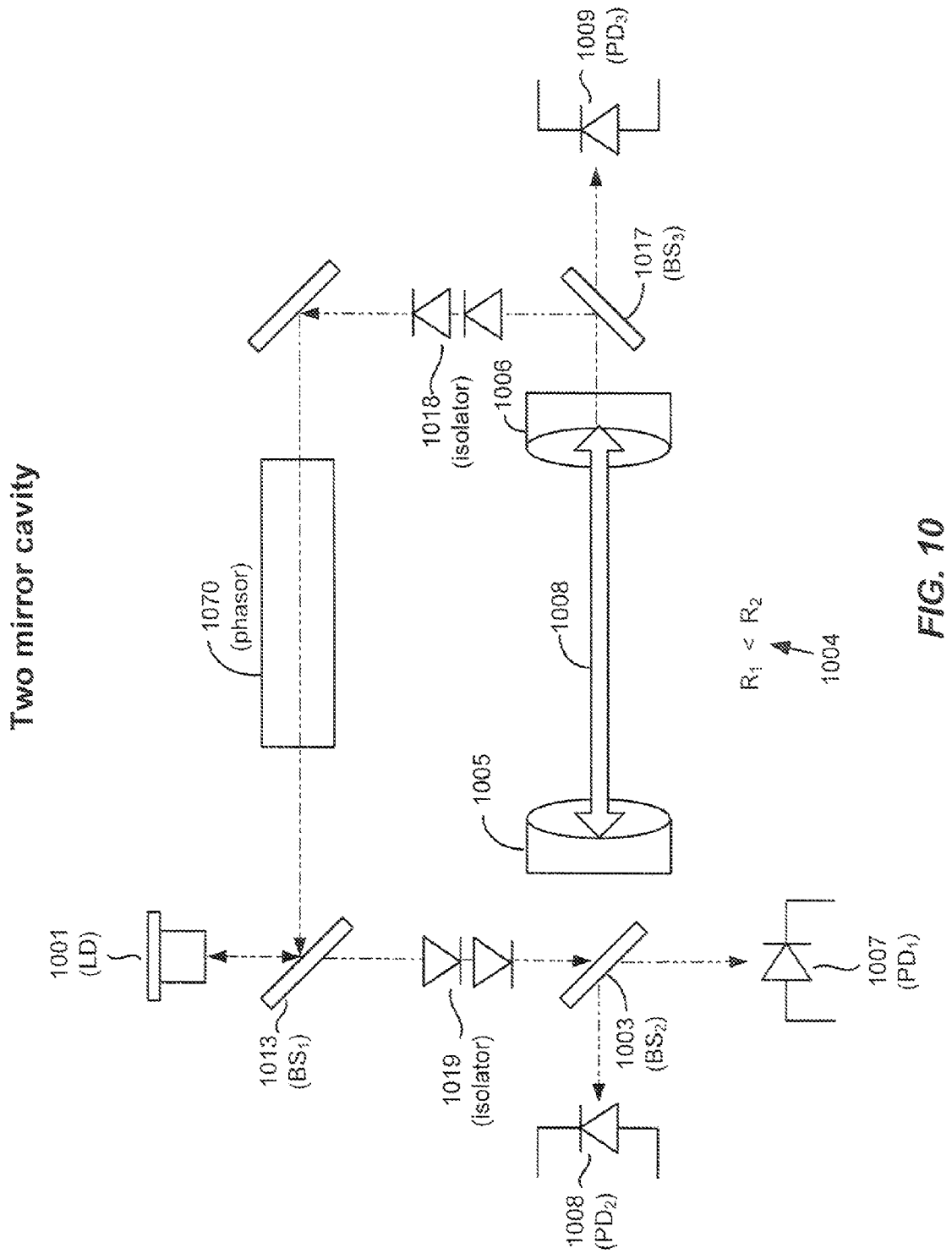
FIG. 10. illustrates a CEAS system having a linear cavity configuration according to another embodiment.

FIG. 10 illustrates a cavity enhanced absorption spectroscopy (CEAS) system 1000 according to yet another embodiment. The principle of operation of CEAS system 1000 is similar to that of CEAS system 100 and 200, for example, including a linear cavity structure 1004, with cavity mirror 1005 being a cavity coupling mirror. Cavity coupling mirror 1005 is positioned such that incident light beam 1012 generated by laser diode source 1001 impinges upon mirror 1005 perpendicular to the plane defined by mirror 1005 at the area of impact, so that light is reflected to photodetector 1008 (through beamsplitter 1003). Beamsplitting element 1003 allows a portion 1013 of incident beam 1012 to pass to detector 1007 and reflects the remainder to mirror 1005. Photodetector 1009, in this embodiment, is positioned to receive and detect the portion of the intra-cavity light 1018 circulating within cavity 1004 between mirrors 1005 and 1006 that emerges or escapes via mirror 1006. Similar to the operation of CEAS 100, photodetector 1007 detects and generates a signal representing the intensity of the laser light 1012 incident on the cavity coupling mirror 1005, detector 1008 detects and generates a signal representing the intensity of the laser light reflected by the cavity coupling mirror 1005, and detector 1009 detects and generates a signal representing the intra-cavity optical power of light circulating in the cavity 1004. An intelligence module (not shown) receives the three detector output signals and processes these signals to produce or generate a normalized signal that is a linear function of total cavity loss and that is not sensitive to laser-cavity coupling.

Also as shown in FIG. 10 are additional elements to enhance control of the optical feedback, specifically control of the optical feedback to source 1001. As shown, a portion of light emerging from cavity mirror 1006 is directed by beamsplitting element 1017 through a phasor 1020 (or other adjustable light attenuating element) and returns to source 1001, via beamsplitting element 1013. Optical isolators 1018 and 1019 are provided to completely block light which travels in the opposite direction. For example, optical isolator element 1019 blocks light returning (e.g., reflected light or light escaping from the cavity via mirror 1005) from mirror 1005 toward source 1001 and optical isolator element 1018 prevents light returning from phasor 1020 (e.g., light reflected by phasor 1020 or source light reflected by beamsplitter 1013 that is passing through phasor 1020 on an opposite path) from impinging on mirror 1006. Selection of the cavity mirror reflectivities (e.g., $R_1$ and $R_2$) defines the optical feedback intensity provided to source 1001. Use of phasor 1020 advantageously allows for phase control of the optical feedback provided to source 1001 from the cavity 1004.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A system for detecting one or more analyte species present in a gaseous or liquid medium, the system comprising:
    a laser that emits continuous wave laser light;
    a resonant optical cavity containing said medium and having at least two cavity mirrors, one of which is a cavity coupling mirror;
    mode matching optics configured to couple the laser light to the cavity via the cavity coupling mirror;
    a first detector configured to measure an intensity of the laser light incident on the cavity coupling mirror and to generate a first signal representing the intensity of the laser light incident on the cavity coupling mirror;
    a second detector configured to measure an intensity of the laser light reflected by the cavity coupling mirror and to generate a second signal representing the intensity of the laser light reflected by the cavity coupling mirror;
    a third detector configured to measure an intensity of the intracavity optical power of light circulating in the cavity and to generate a third signal representing the intracavity optical power of light circulating in the cavity; and
    an intelligence module that processes the first, second and third signals and produces a normalized output signal that is a linear function of total cavity loss and that is not sensitive to laser-cavity coupling.

2. The system of claim 1, wherein the third detector includes a photodetector located external to the cavity and configured to produce a signal proportional to the intracavity optical power by detecting the intensity of light emerging from a cavity mirror.

3. The system of claim 1, wherein the third detector includes a photodetector located internal to the cavity and configured to obtain a signal proportional to the intracavity optical power by detecting the intensity of light scattered by one of the cavity mirrors.

4. The system of claim 1, wherein the third detector includes a photodetector located internal to the cavity and configured to obtain a signal proportional to the intracavity optical power by detecting the intensity of light scattered by said medium within the cavity.

5. The system of claim 1, wherein each of the first, second and third detectors includes a photodetector that outputs a signal proportional to the intensity of light detected.

6. The system of claim 1, wherein the cavity is a ring cavity having three or more cavity mirrors.

7. The system of claim 1, wherein the cavity is a linear cavity having two cavity mirrors.

8. The system of claim 1, wherein the cavity is a V-shaped cavity having three cavity mirrors.

9. The system of claim 1, wherein the cavity is capable of being scanned whereby an optical frequency of a cavity resonance peak is adjustable over a range of frequencies.

10. The system of claim 9, further including a means for controlling a position of one of the cavity mirrors so as to scan the optical frequency of the cavity resonance peak.

11. The system of claim 1, wherein the laser includes a semiconductor laser that is sensitive to optical feedback from light impinging on the laser from the cavity coupling mirror, the system further including a means for adjusting a phase of the light impinging on the laser from the cavity coupling mirror.

12. The system of claim 1, wherein the laser is capable of being scanned whereby a mean optical frequency of the laser is adjustable over a range of frequencies.

13. The system of claim 12, further including means for adjusting the mean optical frequency of the laser so as to scan the mean optical frequency of the laser over a cavity resonance peak.

14. The system of claim 1, wherein the intelligence module produces the normalized signal by calculating a ratio of the difference between the intensity of the laser light incident on the cavity coupling mirror and the intensity of the laser light reflected by the cavity coupling mirror to the intensity of the intracavity optical power of light circulating in the cavity.

15. A method of detecting one or more analyte species present in a gaseous or liquid medium using a laser that that emits continuous wave laser light and a resonant optical cavity containing said medium and having at least two cavity mirrors, one of which is a cavity coupling mirror, the method comprising:
    coupling the laser light to the cavity via the cavity coupling mirror using mode matching optics;
    measuring an intensity of the laser light incident on the cavity coupling mirror generating a first signal representing the intensity of the laser light incident on the cavity coupling mirror;
    measuring an intensity of the laser light reflected by the cavity coupling mirror and generating a second signal representing the intensity of the laser light reflected by the cavity coupling mirror;
    measuring an intensity of the intracavity optical power of light circulating in the cavity and generating a third signal representing the intensity of the intracavity optical power of light circulating in the cavity; and
    processing the first, second and third signals to produce a normalized signal that is a linear function of total cavity loss and that is not sensitive to laser-cavity coupling.

16. The method of claim 15, wherein the normalized signal is produced by calculating a ratio of the difference between the intensity of the laser light incident on the cavity coupling mirror and the intensity of the laser light reflected by the cavity coupling mirror to the intensity of the intracavity optical power of light circulating in the cavity.

17. The method of claim 15, wherein measuring an intensity of the intracavity optical power of light circulating in the cavity is performed using a photodetector located external to the cavity, and wherein the photodetector measures the intensity of light emerging from a cavity mirror.

18. The method of claim 15, wherein measuring an intensity of the intracavity optical power of light circulating in the cavity is performed using a photodetector located internal to the cavity, and wherein the photodetector measures the intensity of light scattered by one of the cavity mirrors.

19. The method of claim 15, wherein measuring an intensity of the intracavity optical power of light circulating in the cavity is performed using a photodetector located internal to the cavity, and wherein the photodetector measures the intensity of light scattered by said medium within the cavity.

20. The method of claim 15, wherein the cavity is a ring cavity having three or more cavity mirrors.

21. The method of claim 15, wherein the cavity is a V-shaped cavity having three cavity mirrors.

22. The method of claim 15, wherein the cavity is a linear cavity having two cavity mirrors.

23. The method of claim 15, further including scanning an optical frequency of a cavity resonance peak over a range of frequencies.

24. The method of claim 23, wherein scanning includes controlling a position of one of the cavity mirrors so as to scan the optical frequency of the cavity resonance peak.

25. The method of claim 15, further including scanning a mean optical frequency of the laser over a range of frequencies.

26. The method of claim 25, wherein scanning includes adjusting the mean optical frequency of the laser so as to scan the mean optical frequency of the laser over a cavity resonance peak.

27. A system for detecting one or more analyte species present in a gaseous or liquid medium, the system comprising:
    a laser that emits continuous wave laser light;
    a resonant optical cavity defined by at least two cavity mirrors, one of which is a cavity coupling mirror, wherein said medium is located within the cavity;
    mode matching optics configured to couple the laser light to the cavity via the cavity coupling mirror;
    a first means for measuring an intensity of the laser light incident on the cavity coupling mirror and for generating a first signal representing the intensity of the laser light incident on the cavity coupling mirror;
    a second means for measuring an intensity of the laser light reflected by the cavity coupling mirror and for generating a second signal representing the intensity of the laser light reflected by the cavity coupling mirror;
    a third means for measuring an intensity of the intracavity optical power of light circulating in the cavity and for generating a third signal representing the intracavity optical power of light circulating in the cavity; and
    a means for processing signals received from the first, second and third means for measuring to produce a normalized signal that is a linear function of total cavity loss and that is not sensitive to laser-cavity coupling.

28. The system of claim 27, wherein the means for processing produces the normalized signal by calculating a ratio of the difference between the intensity of the laser light incident on the cavity coupling mirror and the intensity of the laser light reflected by the cavity coupling mirror to the intensity of the intracavity optical power of light circulating in the cavity.

* * * * *